United States Patent [19]

Bonnem

[11] Patent Number: 5,178,855
[45] Date of Patent: Jan. 12, 1993

[54] TREATMENT OF LUEKOCYTE DYSFUNCTION WITH GM-CSF

[75] Inventor: Eric M. Bonnem, Plainfield, N.J.

[73] Assignee: Schering Corporation, Kenilworth, N.J.

[21] Appl. No.: 721,586

[22] PCT Filed: Jan. 26, 1990

[86] PCT No.: PCT/US90/00379
§ 371 Date: Jul. 17, 1990
§ 102(e) Date: Jul. 17, 1990

[51] Int. Cl.$^5$ ............................................. A61K 37/02
[52] U.S. Cl. .................................................. 424/85.1
[58] Field of Search ...................................... 424/85.1

[56] References Cited

FOREIGN PATENT DOCUMENTS 8702060 4/1987 World Int. Prop. O. .
8703204 6/1987 World Int. Prop. O. .
8706954 11/1987 World Int. Prop. O. .
8800832 2/1988 World Int. Prop. O. .

OTHER PUBLICATIONS

Weisbart et al., Nature, vol. 332, Apr. 14, 1988 pp. 647-648.
Weisbart, Richard H. et al., Nature vol. 314, Mar. 28, 1985 pp. 361-363.
Metcalf, Donald, Science, vol. 229, Jul, 5, 1985, pp. 16-22.
Gasson, Judith C. et al., Leukemia: Recent Advances in Biology and Treatment, 1985, pp. 257-265.
Metcalf, Donald, Blood, vol. 67, No. 2 Feb. 1986, pp. 257-267.
Fleischmann, Jacob et al., Blood, vol. 68, No. 3 Sep. 1986 pp. 708-711.
Burgess, Anthony W. et al., Blood, vol. 69, No. 1, Jan. 1987 pp. 43-51.
Clark, S.C. et al., Science, vol. 236, Jun. 5, 1987, pp. 1229-1230.
Groopman, Jerome E., et al., The New England Journal of Medicine, vol. 317, No. 10, Sep. 3, 1987, pp. 593-598.
Baldwin, G. C. et al., Selected Abstracts on Hematopoietic Growth Factors from The American Society of Hematology, p. 78.
English, D., Selected Abstracts on Hematopoietic Growth Factors from The American Society of Hematology, p. 80.
Linnekin, D. M. et al., Selected Abstracts on Hematopoietic Growth Factors from The American Society of Hematology, p. 53.
Sullivan, R., et al., Selected Abstracts on Hematopoietic Growth Factors from the American Society of Hematology, p. 21.
Coffey, R. G. et al., The Journal of Immunology, 140, No. 8 Apr. 15, 1988 pp. 2695-2701.
Vadhan-Raj, S. Blood, vol. 72, No. 1 Jul. 1988, pp. 134-141.
Antin, Joseph H. et al., Blood, vol. 72, No. 2, Aug. 1988, pp. 705-713.
Coleman, David L., et al., Blood, vol. 72, No. 2, Aug. 1988, pp. 573-578.
Antman, Karen S. et al., The New England Journal of Medicine, vol. 319, No. 10, Sep. 8, 1988, pp. 594-598.
In the News, Abstract of Investor's Daily, p. 1, Oct. 14, 1988.
News Release—Schering-Plough, Nov. 17, 1988.
F-D-C Reports, Nov. 21, 1988.
"Researchers Discover Anti-Cholesterol Drug by Accident", Health Week, Cheryville, Calif., Dec. 27, 1988.
"Expectations Still Flying High for Blood Colony Stimulators" Medical World News, Jan. 23, 1989 p. 13.
Kurland, Jeffrey et al., Proc. Natl. Acad. Sci. vol. 76, No. 5, pp. 2326-2330.
Burgess, A. W. et al., Blood, vol. 56, No. 6, Dec. 1980, pp. 974-958.
Atkinson, Y.H. et al., Immunology, 64, pp. 519-525, 1988.
Brandt, S. J. et al., The New England Journal of Medicine, vol. 318, No. 14, Apr. 7, 1988.
Hancock, W.W. et al., The Journal of Immunology, vol. 140, No. 9, May 1, 1988 pp. 3021-3025.

Primary Examiner—Merrell C. Cashion, Jr.
Assistant Examiner—Choon Koh
Attorney, Agent, or Firm—Paul G. Lunn; Norman C. Dulak; James R. Nelson

[57] ABSTRACT

A method of treating leukocyte dysfunction in a mammal, preferably a human, wherein said dysfunction is associated with pyhsical trauma, is disclosed. Preferably the method is used wherein the dysfunction is associated with thermal injury. The method comprises administering to the mammal an effective amount of GM-CSF to potentiate the function of the dysfunctional leukocytes.

The use of GM-CSF for the manufacture of a medicament for use in treating a patient having such leukocyte dysfunction and a pharmaceutical composition comprising GM-CSF for use in such treating are also disclosed.

22 Claims, 5 Drawing Sheets

TREATMENT OF LUEKOCYTE DYSFUNCTION WITH GM-CSF

This invention relates to the treatment of leukocyte dysfunction associated with physical trauma, particularly thermal injury, by administering effective doses of GM-CSF.

GM-CSF is a lymphokine (stimulator of the immune system) that exhibits a broad spectrum of immune cell stimulation as described in Burgess and Metcalf, *Blood*, 56:947 (1980) and Metcalf, *Blood* 67:257 (1986). GM-CSF has been shown to increase the leukocyte count in patients with acquired immunodeficiency syndrome [Brandt et al., *N. Engl. J. Med.*, 318:869 (1988)] and people suffering from chemotherapy-induced myelosuppression [Antman et al., *New Engl. J. Med.*, 319:593 (1988), and it has been suggested that various colony stimulating factors alone or in combination with erythropoietin and/or an antiviral agent and/or interleukin-2 (IL-2) may be useful for the treatment of patients suffering form AIDS-type disease (PCT Application No. 87/03204).

Although GM-CSF was identified because of its ability to stimulate proliferation of hematopoietic precursor cells, it is also able to stimulate a number of functional aspects of mature granulocytes and macrophages. These effects include synthesis of biologically active molecules such as prostaglandin E [Hancock et al., *J. Immunol.*, 140:3021 (1988) and Kurland et al., *Proc. Natl. Acad. Sci. USA*, 76:2326 (1979)]; increased phagacytic activity [Weisbart et al., *Nature*, 332:647 (1988)]; expression and/or affinity of various membrane markers such as the IL-2 receptor [Hancock et al., *J. Immunol.*, 140:3021 (1988)] and the bacterial product formylmethionylleucylphenylalanine receptor on neutrophils, which receptors elicit the production of superoxide anions [Atkinson et al., *Immunology*, 64:519 (1988)]; and the regulation of enzyme activity such as the stimulation of guanylate cyclase and the inhibition of adenylate cyclase [Coffey et al., *J. Immunol.*, 140:2695 (1988)].

In cases of physical trauma, such as thermal injury, there is an associated dysfunction of the white blood cells (WBC), particularly monocytes and leukocytes. Thus, although there may be sufficient numbers of WBC to function—i.e., engage in phagocytosis and superoxide generation—if operating normally, because of the leukocyte dysfunction there if a malfunction or suppression of the immune system. The immune system malfunction is attributable to the leukocyte dysfunction rather than to there being an insufficient number of leukocytes.

Those skilled in the art will appreciate that such leukocyte dysfunction jeopordizes the recovery of the physical trauma patient. For example, in the thermal burn patient such dysfunction can result in a greater risk of infection. To date no significant impact has been made in treating leukocyte dysfunction in vivo in thermal injury (burn) patients and the associated clinical consequences such as infection.

A welcome contribution to the art would be a method of treating leukocyte dysfunction associated with physical trauma, particularly thermal injury. Such a contribution is provided by this invention.

The invention may be summarized in the following manner. It has surprisingly and unexpectedly been discovered that leukocyte dysfunction associated with physical trauma, particularly thermal injury, can effectively be treated by the administration of GM-CSF. It has been discovered that GM-CSF administered to thermal injury patients results in increased leukocyte function—i.e., there is a potentiation of leukocyte function. Such treatment therefore result sin a significantly higher response to infection in thermal injury patients. The potentiation in vivo of leukocyte function with GM-CSF is to be distinguished from merely increasing the umber of dysfunctioning leukocytes. Since leukocyte dysfunction is also present in other types of physical trauma besides thermal injury, it is contemplated that leukocyte dysfunction associated with these other types of physical trauma are likewise treatable with GM-CSF.

Thus, in one embodiment this invention provides a method of treating leukocyte dysfunction in mammals, including humans, associated with physical trauma by the administration of an effective amount of GM-CSF to potentiate the function of said leukocytes.

In another embodiment this invention provides a method of treating leukocyte dysfunction in mammals, including humans, associated with thermal injury by the administration of an effective amount of GM-CSF to potentiate the function of said leukocytes.

This invention also provides the use of GM-CSF for the manufacture of a medicament for use i a method of treating a mammal having leukocyte dysfunction that is associated with physical trauma such as thermal injury by administering to said mammal an effective amount of GM-CSF to potentiate the function of said leukocytes.

This invention also provides the sue of GM-CSF for treating a patient having leukocyte dysfunction that is associated with physical trauma such as thermal injury.

This invention further provides a pharmaceutical composition comprising GM-CSF for use in treating a patient having leukocyte dysfunction associated with physical trauma such as thermal injury.

Figure 1:
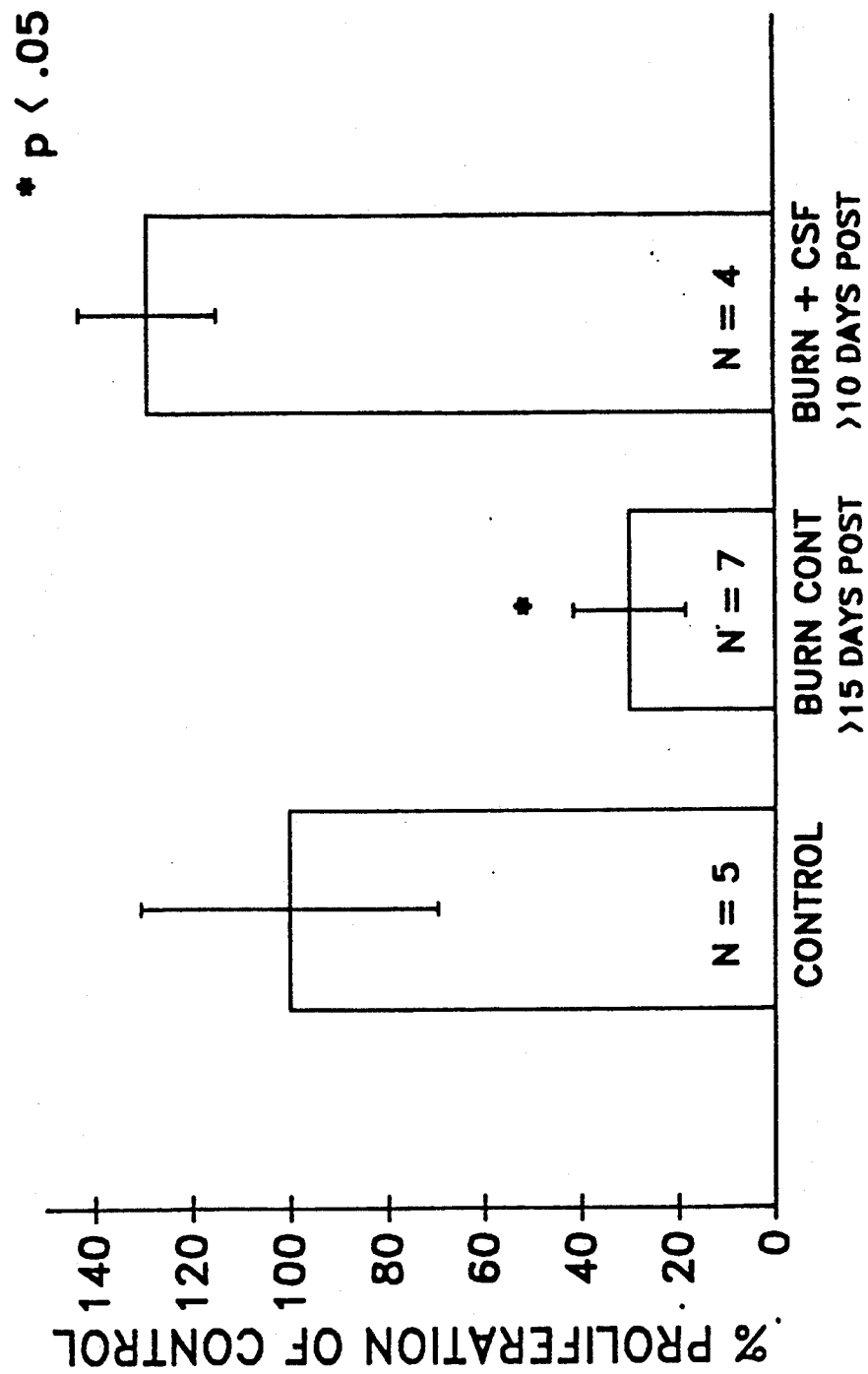
FIG. 1 is a graphical presentation of enhance proliferation of monocytes in patients with thermal injury who were treated with GM-CSF.

Preferably the mammals treated will be humans and the GM-CSF utilized will be one of the human allotypes.

In a particularly preferred embodiment an effective amount of the GM-CSF is administered intravenously, such as by injection or infusion, over a time sufficient to allow the GM-CSF to potentiate leukocyte function without significant loss in GM-CSF activity (such as by metabolism of the Gm-CSF). In general the effective amount is about 3 to about 30 micrograms of GM-CSF per kilogram of body weight per day which is administered by intravenous infusion over a time period of about 30 minutes to about 24 hours. Preferably the effective amount is about 3 to about 15 micrograms per kilogram of body weight which is administered by intravenous infusion over a time period of about 2 to about 6 hours with about 2 to about 4 hours being more preferably and about 4 hours being most preferably. Most preferably, the dosages utilized are 3, 10, or 15 micrograms per kilogram of body weight per day. The actual dosage may be varied depending on the patient's weight and tolerance to the GM-CSF.

Unless stated otherwise, the term "physical trauma" as used herein refers to trauma to the various tissues and organs of the body including organ systems, musculature, the skeletal system, the vascular system, and the like. The trauma may result from any mechanism or mode of action sufficient to cause injury, such as for example, thermal injury (burn), electrical burn, chemical burn, blunt trauma such as that resulting from accident or assault, traumatic amputation, and the like.

Unless stated otherwise, the term "thermal injury" as used herein means the physiological insult to an individual caused by excessive heat, as distinguished from electric and chemical burns.

Unless stated otherwise, the term "leukocyte dysfunction" as used herein means that the leukocytes, e.g., monocytes, have a significantly reduced functional capability or complete failure of their ability to protect the human from overwhelming infection. Some of the function so monocytes and granulocytes include in vitro or in vivo demonstrations of phagocytosis and/or superoxide generation.

Unless stated otherwise, the term "leukocyte function" as used herein refers to the normal functioning of the leukocytes, e.g., monocytes, in their engagement in phagocytosis and/or superoxide generation.

Unless stated otherwise the term "leukocyte" as used herein has its generally art recognized meaning and therefore includes the different cellular types that are classified as being white blood cells including, for example, cells of the myeloid, lymphoid, and monocytic series.

This invention provides a method for potentiating leukocyte function in dysfunctional leukocytes in mammals, wherein such dysfunction is associated with thermal injury or other forms of physical trauma. In this method an effective amount of GM-CSF is administered over a time period sufficient to effect increased leukocyte function. In effect, the method of this invention significantly reduces or reverses the dysfunction of the leukocytes.

Any suitable GM-CSF may be employed in the present invention. Complementary DNAs (CDNAs) for GM-CSF have recently been cloned and sequenced by a number of laboratories, e.g. Gough et al., *Nature*, 309:763 (1984)(mouse); Lee et al., *Proc. Natl. Acad. Sci. USA*, 82:4360 (1985)(human); Wong et al., *Science*, 228:810 (1985) (human and gibbon); Cantrell et al., *Proc. Natl. Acad. Sci. USA*, 82:6250 (1985)(human). Moreover, non-recombinant GM-CSF has been purified from various culture supernatants, e.g., Burgers et al., *Exp. Hematol.*, 9:893 (1981)(mouse); Sparrow et al., *Exp. Hematol.*, 12:267 (1984)(rat); Gasson et al., *Science*, 230:1171 (1985)(human); Burgess et al., *Blood*, 69:43 (1987)(human). Among the human GM-CSFs, nucleotide sequence and amino acid sequence heterogeneity have been observed. For example, both threonine and isoleucine have been observed at position 100 of human GM-CSF with respect to the N-terminal alanine, suggesting that allelic forms, or polymorphs, of GM-CSF may exist within human populations. Also, various leader sequences may occur at the N-terminal position of the amino acid sequence. These leader sequences may be of various lengths and amino acid composition, which may or may not affect biological activity. Preferably, the GM-CSF used in the present invention for treating humans will be a human GM-CSF (hGM-CSF), most preferably the recombinant human GM-CSF (rhGM-CSF) described in Lee et al., *Proc. Natl. Acad. Sci. USA*, 82:4360 (1985), as purified in U.S. patent application Ser. No. 111,886, filed Oct. 23, 1987. All of the above discussed references are incorporated herein by reference for their disclosures of representative GM-CSFs suitable for use in the present invention including their DNA and amino acid sequences and for their disclosures of methods for producing and purifying GM-CSF.

According to this invention, mammals are administered an effective amount of GM-CSF. An effective amount is that amount required to potentiate the function of the dysfunctional leukocytes. Preferably, as stated previously, the mammal is a human and the preferred GM-CSF is recombinant human GM-CSF (rhGM-CSF). Generally, an amount of GM-CSF of about 3 to about 30 micrograms per kilogram of body weight per day is sufficient in most patients to produce the desired potentiation of function in the dysfunctional leukocytes. Preferably about 3 to about 25 micrograms per kilogram of body weight is administered per day with about 3 to about 15 micrograms per kilogram being more preferable, and dosages of 3, 10, or 15 micrograms per kilogram being most preferable. An even more preferable dose is 10 micrograms per kilogram.

The GM-CSF is most effective when administered so that there is an effective level of GM-CSF in the blood maintained over a period of time as opposed to rapid administration which results in a sudden increase n GM-CSF blood levels followed by a rapid decrease in GM-CSF blood levels due to metabolism of the GM-CSF. Generally, administration by intravenous bolus and/or infusion over a time period of from about 30 minutes to about 24 hours is sufficient. Preferably such administration is done over a time period of about 2 to about 6 hours, more preferably about 2 to about 4 hours and most preferably about 4 hours. The GM-CSF may also be administered intramuscularly, subcutaneously, topically by direct application to an open injury site, transdermally, nasally (nasal spray), orally(oral spray), by insufflation and the like. Thus, any method of administering an effective dose to provide effective blood levels over a period of time is contemplated.

The GM-CSF, preferably rhGM-CSF, may be prepared in any number of conventional dosage forms such as for example, parenteral, including sterile solutions or suspensions; topical dosage forms such as creams, ointments, lotions, transdermal devices (e.g., of the conventional reservoir or matrix patch type); and the like.

The formulations and pharmaceutical compositions contemplated by the above dosage forms can be prepared with conventional pharmaceutically acceptable excipients and additives, using conventional techniques.

Presently, the GM-CSF, preferably recombinant human rhGM-CSF, is administered via the intravenous route. The solutions to be administered may be reconstituted from lyophilized powders and they may additionally contain preservatives, buffers, dispersants, etc. Preferably, rhGM-CSF is reconstituted with any isotonic medium normally utilized for intravenous injection, e.g., preservative-free sterile water. The maximum concentration of rhGM-CSF preferably should not exceed 1500 micrograms per milliliter. Administration may be accomplished by continuous intravenous infusion or by intravenous injection. For continuous infusion, the daily dose can be added to normal saline and the solution infused by mechanical pump or by gravity.

The following examples are illustrative only and should not be construed as limiting the invention in any way. Those skilled in the art will appreciate that variations are possible which are within the spirit and scope of the appended claims.

The effect of GM-CSF on potentiating the function of dysfunctional leukocytes in patients suffering from thermal injury over 20% to 70% of their body surface area can be determined by the following test protocol: Initially patients age 18 or older with thermal injury over 20 to 40% of their body surface area, in whom cardiovascular stabilization has taken place or was ongoing, and without inhalation injury to the lungs, were treated with recombinant human rhGM-CSF within 48 hours of injury. Thereafter patients age 18 or older with thermal injury over 40 to 70% of their body surface area, in whom cardiovascular stabilization has taken place or was ongoing and without inhalation injury, would be treated with rhGM-CSF within 48 hours of injury. Thereafter, patients age 18 or older with thermal injury over 40 to 70% of their body surface area, in whom cardiovascular stabilization has taken place or was ongoing and with mild to moderate inhalation injury (as diagnosed by physical exam on xenon scan) but without bronchoscopic evidence of inhalation injury will be treated with rhGM-CSF within 48 hours of injury. The rhGM-CSF was obtained as described in Lee et al., Proc. Natl. Acad. Sci. USA, 82:4360 (1985) and U.S. patent application Ser. No. 111,886, filed Oct. 23, 1987. The rhGM-CSF was in the form of a lyophilized powder and was prepared for intravenous administration by the attending physician or pharmacist by diluting to 1 ml with sterile water then to this resulting solution there was added 50 ml of normal saline. The patients were more preferably administered rhGM-CSF in doses of 3, 10, or 15 micrograms per kilogram of body weight intravenously (bolus or infusion) over a 2 hr to 4 hour time period, most preferably 4 hours, once a day. Each dose level of GM-CSF was administered to groups of 3 to 5 patients.

Blood samples were taken for in vitro analysis to determine leukocyte function. The blood samples were analyzed by methods known in the art. An increase in white blood cell counts of 50% or more above baseline is indicative of therapeutic efficacy and clinically meaningful results.

The combined results of all the dosage levels are given in FIGS. 1 to 5. In FIGS. 1 to 5 "Normal" or "Control" refers to the results with a normal population of patients—i.e., no thermal injury—, "Burn Control" refers to a population of patients with thermal injury and no GM-CSF treatment. In FIGS. 2 to 5 "Pre" refers to pretreatment—i.e., no administration of GM-CSF—and the numbers "1", "8", and "15" on the x-axis refers to the number o days of treatment with rhGM-CSF.

FIG. 1 represents a comparison of tritiated thymidine incorporation in a group of patients in comparison to a historical control group. As noted in FIG. 1, in the four patient study(n=4) at greater than ten-day post burn, there was a significant enhancement of proliferation of monocytes as manifested by tritiated thymidine incorporation. There are two controls noted in FIG. 1, the far left bar(N=5) indicates normal control with no intracedent illness such as thermal injury and the middle bar(N=7, greater than 15 days post burn) represents a cohort or patients who actually did have thermal injury.

Figure 2:
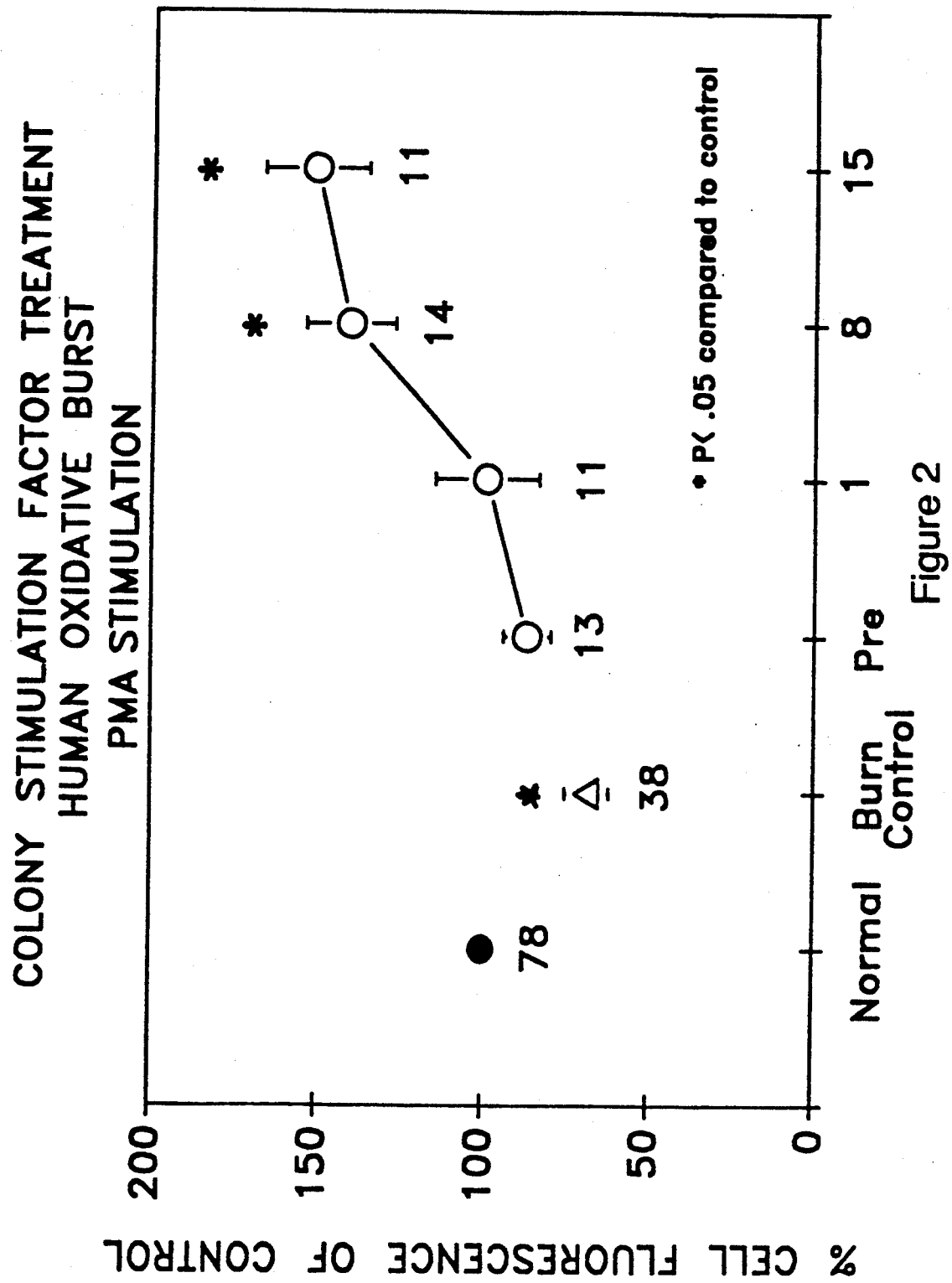
FIGS. 2 and 3 are graphical presentations of enhanced oxidative bursts of monocytes in patients with thermal injury who were treated with GM-CSF.
Figure 3:
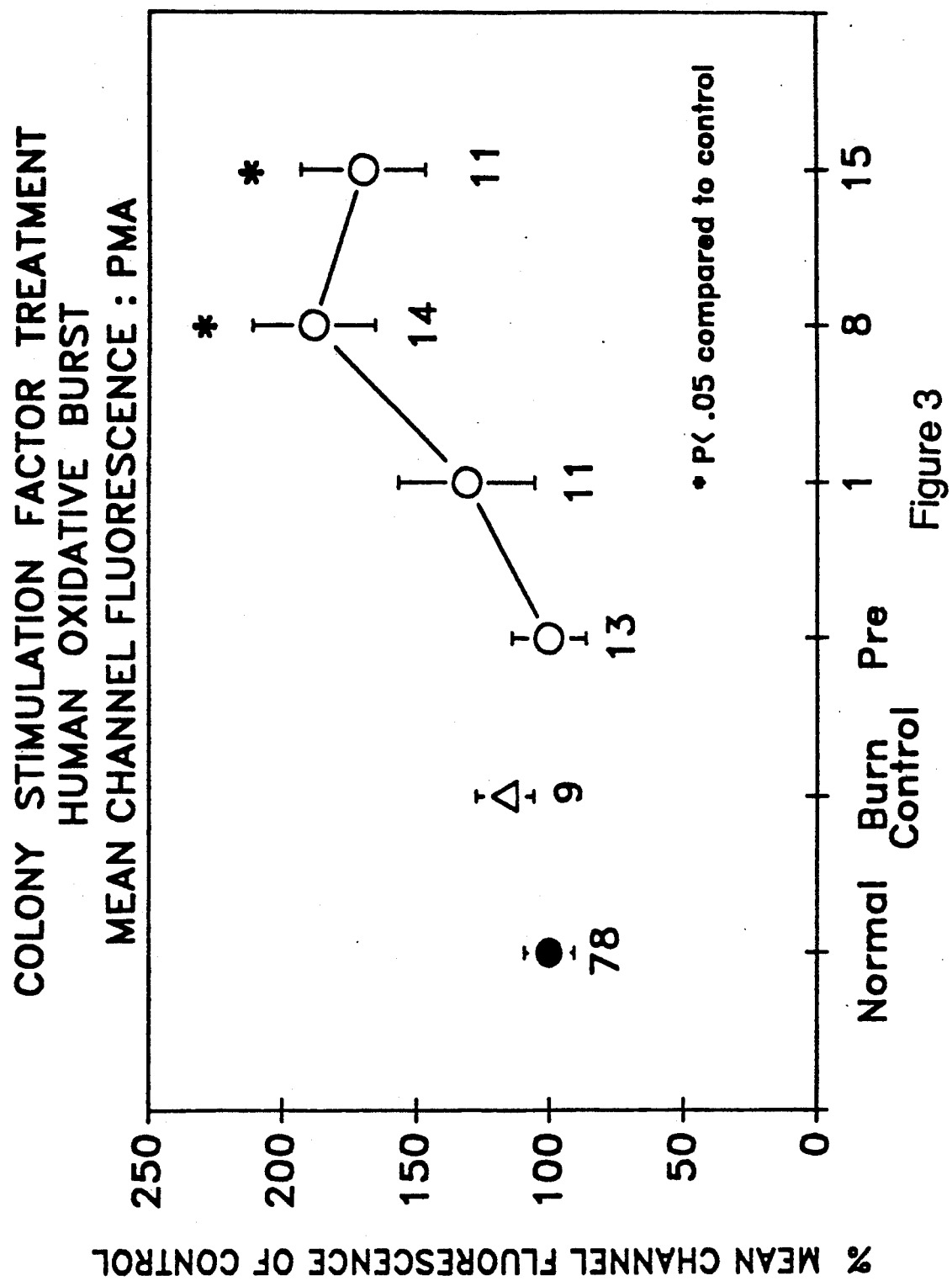

FIGS. 2 and 3 represents the human oxidate of bursts of PMA stimulation of monocytes. These figures attempt to demonstrate that with continued rhGM-CSF administration over a period of 15 days there is an enhancement of oxidative bursts of monocytes.

Figure 4:
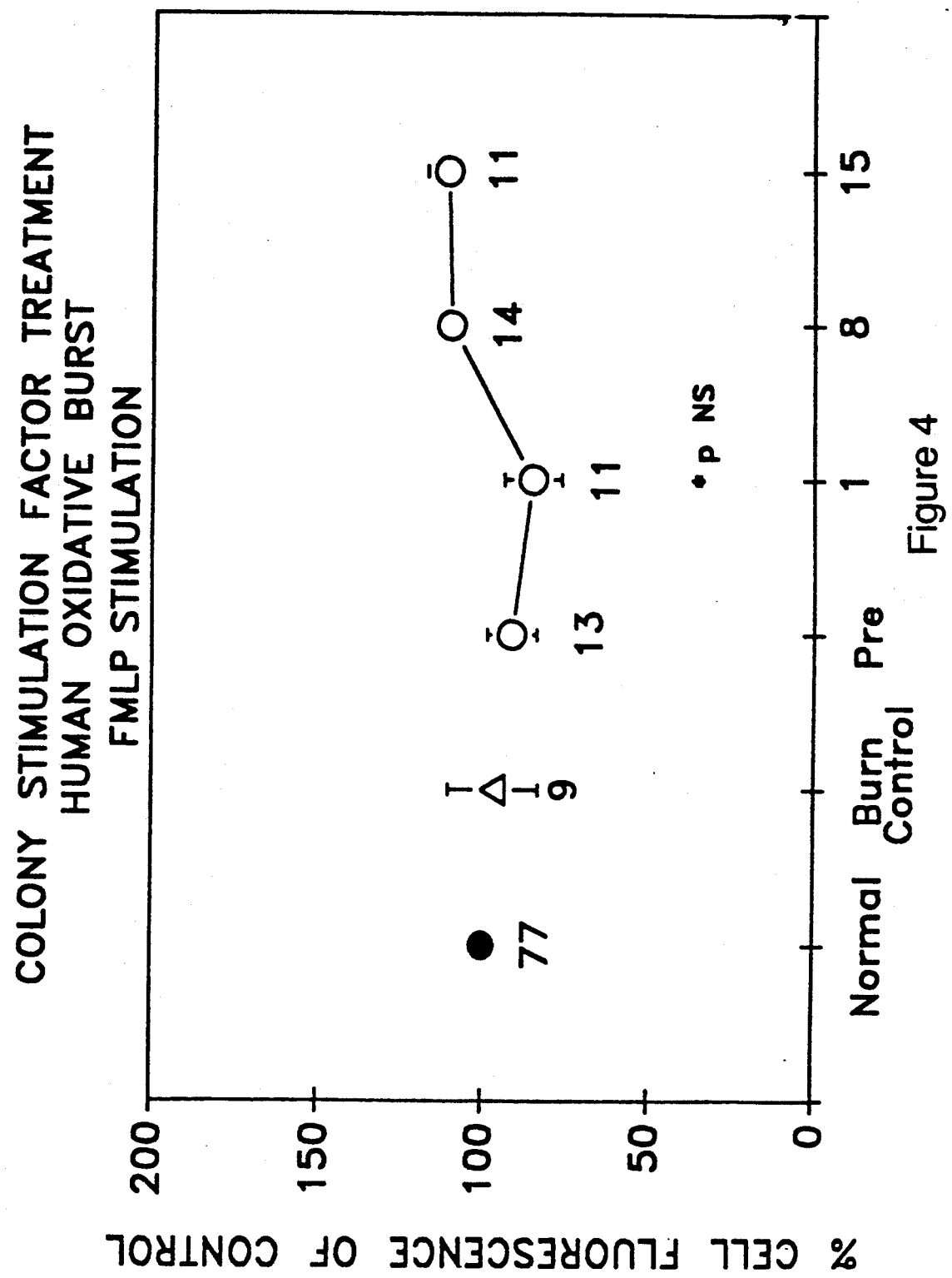
FIGS. 4 and 5 are graphical presentations showing no significant stimulation of oxidative bursts in monocytes over a period of time from FMLP(formylmethionylieucylphenylalanine) alone in patients with thermal injury who were treated with GM-CSF.
Figure 5:
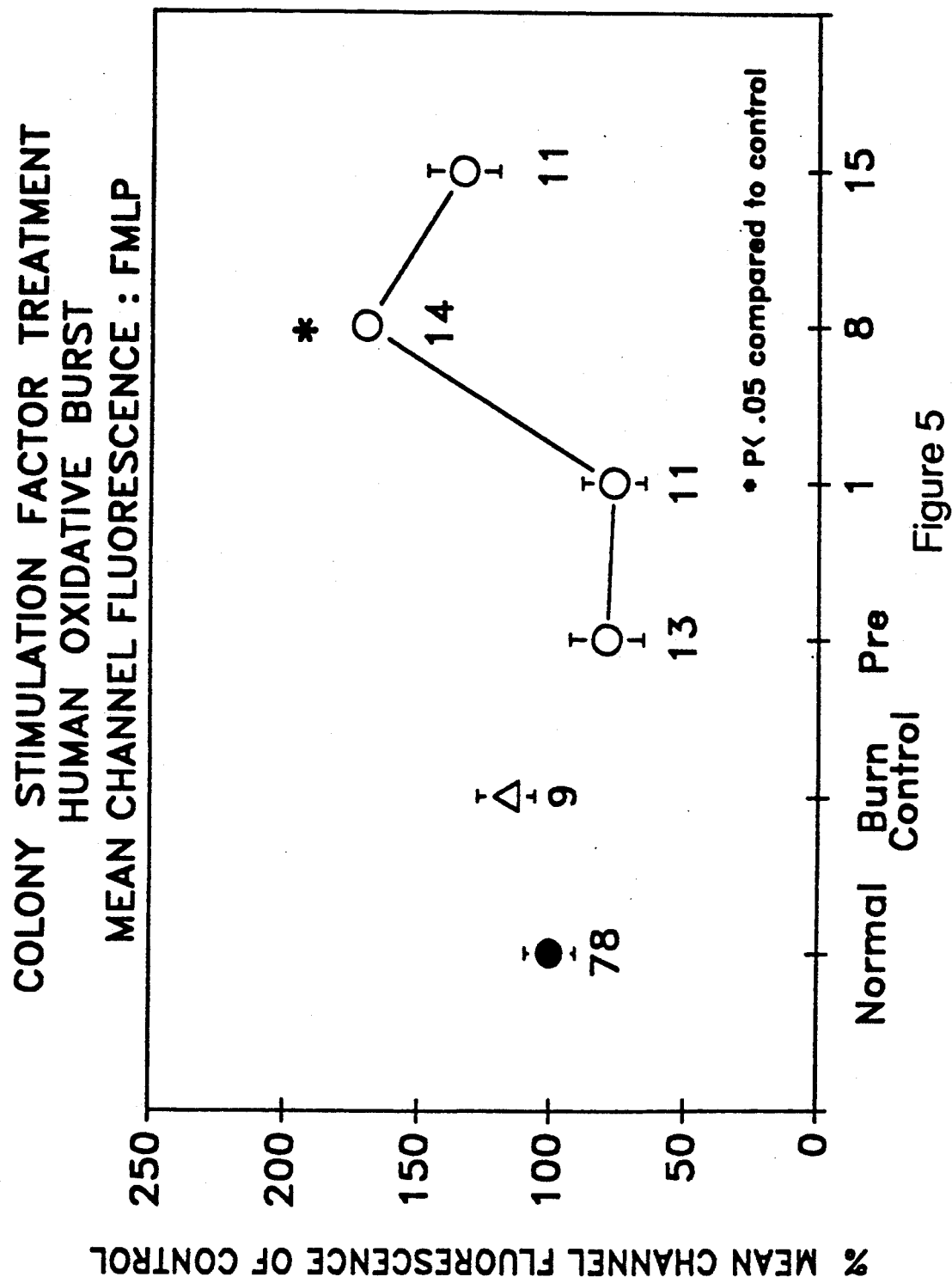

FIGS. 4 and 5 demonstrate FMLP stimulation of human oxidative respiration. These figures demonstrate that over a period of time there is no significant stimulation of oxidative bursts in monocytes from FMLP alone.

The invention being thus described, it will be obvious that the same may be varied in many ways. Such variations are not to be regarded as a departure from the spirit and scope of the invention and all such modifications are intended to be included within the scope of the claims.

What is claimed is:

1. A method for treating leukocyte dysfunction associated with physical trauma in a mammal, comprising administering to a mammal having dysfunctional leukocytes due to physical trauma an amount of GM-CSF effective to potentiate the function of the dysfunctional leukocytes.

2. The method of claim 1 in which the mammal is a human being.

3. The method of claim 2 in which the GM-CSF is human GM-CSF.

4. The method of claim 3 in which the GM-CSF is recombinant human GM-CSF.

5. The method of claim 4 in which the GM-CSF is administered in an amount of about 3 to about 30 micrograms per kilogram of body weight per dose.

6. The method of claim 5 in which the GM-CSF is administered in an amount of about 3 to about 15 micrograms per kilogram of body weight per dose.

7. The method of claim 5 in which the GM-CSF is administered by intravenous infusion or injection.

8. The method of claim 7 in which the dose of GM-CSF is administered daily.

9. The method of claim 8 in which the dose of GM-CSF is administered over a period of about 2 to about 24 hours.

10. The method of claim 9 in which the dose of GM-CSF is administered over a period of about 2 to about 6 hours.

11. The method of claim 10 in which the dose of GM-CSF is administered over a period of about 4 hours.

12. The method of claim 11 in which the physical trauma is thermal injury.

13. The method of claim 12 in which the mammal is a human being.

14. The method of claim 13 in which the GM-CSF is human GM-CSF.

15. The method of claim 14 in which the GM-CSF is recombinant human FM-CSF.

16. The method of claim 15 in which the GM-CSF is administered in an amount of about 3 to about 30 micrograms per kilogram of body weight per dose.

17. The method of claim 16 in which the GM-CSF is administered in an amount of about 3 to about 15 micrograms per kilogram of body weight per dose.

18. The method of claim 16 in which the GM-CSF is administered by intravenous infusion or injection.

19. The method of claim 18 in which the dose of GM-CSF is administered daily.

20. The method of claim 19 in which the dose of GM-CSF is administered over a period of about 2 to about 24 hours.

21. The method of claim 20 in which the dose of GM-CSF is administered over a period of about 2 to about 6 hours.

22. The method of claim 21 in which the dose of GM-CSF is administered over a period of about 4 hours.

* * * * *